United States Patent [19]

Counsell et al.

[11] Patent Number: 4,925,649

[45] Date of Patent: May 15, 1990

[54] RADIOIODINATED DIACYLGLYCEROL ANALOGUES AND METHODS OF USE

[75] Inventors: Raymond E. Counsell; Laurie Strawn, both of Ann Arbor, Mich.

[73] Assignee: The University of Michigan, Ann Arbor, Mich.

[21] Appl. No.: 62,530

[22] Filed: Jun. 12, 1987

[51] Int. Cl.$^5$ ...................... A61K 49/02; A61K 49/00
[52] U.S. Cl. ........................................ 424/1.1; 424/9; 260/408
[58] Field of Search ................ 424/1.1, 9, 5; 260/408; 560/104, 105, 47

[56] References Cited

PUBLICATIONS

Weichert, J. et al. "Lipid Soluble Contrast Agents for Hepatic CT Imaging", Acs Meeting Abstract No. 29, Washington, DC 8/1983.

Primary Examiner—John S. Maples
Attorney, Agent, or Firm—Rohm & Monsanto

[57] ABSTRACT

Novel iodinated and radioiodinated 1,2-diacylglycerol analogues are biological reagents for studying the effect of diacylglycerols in the activation of protein kinase C. This calcium-requiring enzyme may be involved in tumor promotion by phorbol diesters and related compounds. Iodinated and radioiodinated 1,2-diacylglycerol analogues, in accordance with the invention, are useful as imaging agents, such as radiopaques and radiopharmaceuticals, and have the general formula:

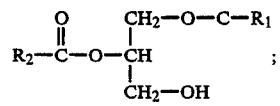

The triglycerol backbone structure is 1,2-disubstituted with one position being occupied by an iodine-containing substituent, preferably an amino-substituted-2,4,6-triiodophenyl aliphatic chain, such as iopanoic acid, or by a monoiodiphenyl aliphatic chain, such as (m-iodophenyl)propanoic acid. The other position may be substituted with saturated and unsaturated long and short aliphatic chains.

14 Claims, 7 Drawing Sheets

FIG. 2
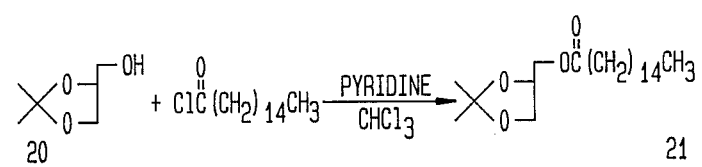
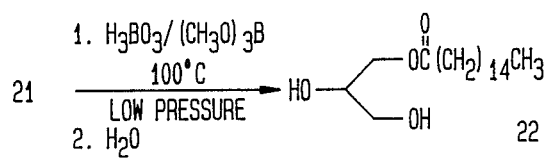
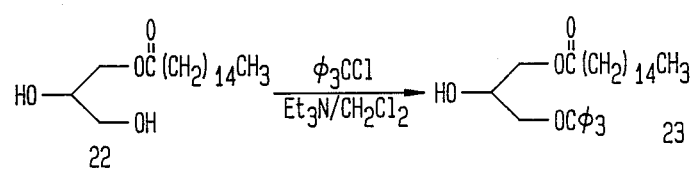
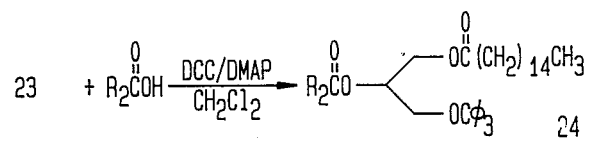
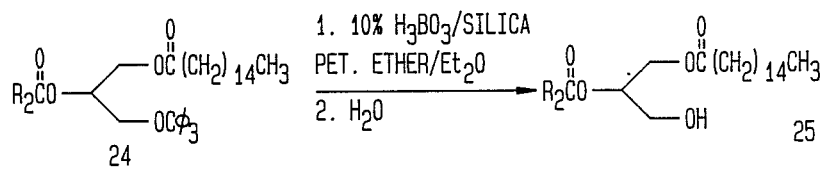

FIG. 4
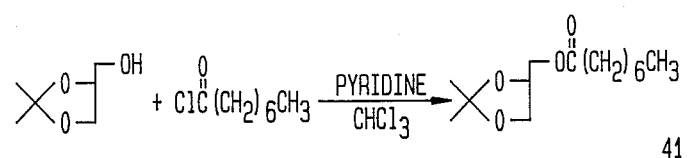
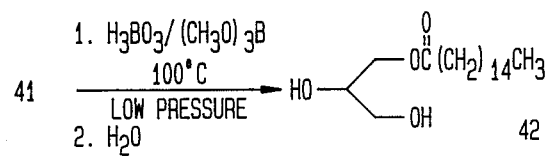
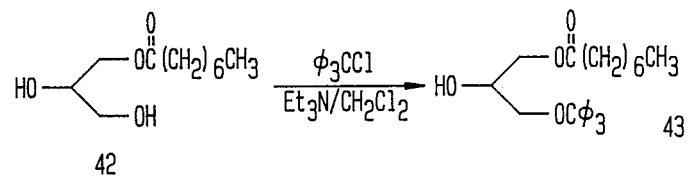
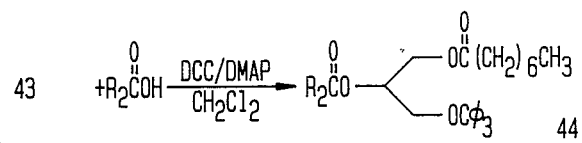
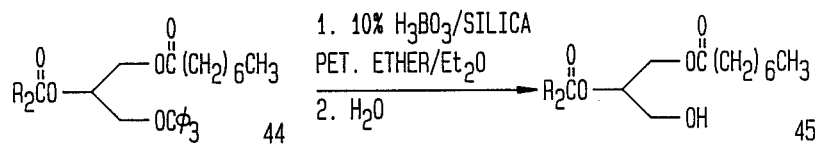

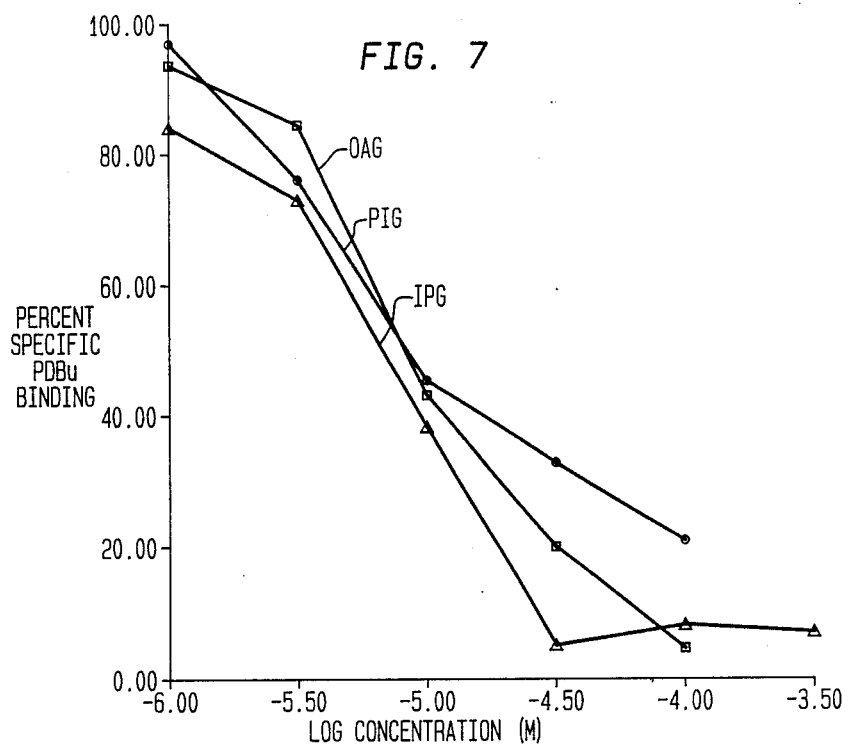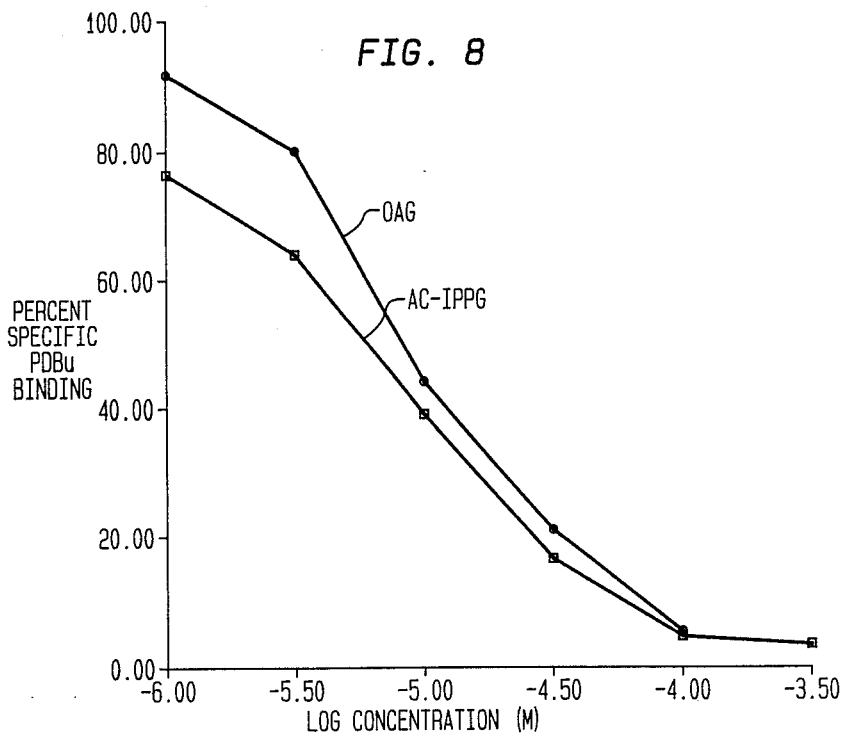

RADIOIODINATED DIACYLGLYCEROL ANALOGUES AND METHODS OF USE this invention was sponsored by the Department of Health and Human Services and the United States Government may have certain rights in this invention.

BACKGROUND OF THE INVENTION

This invention relates to iodinated and radioiodinated compounds which are useful as biological reagents and tracers, and more specifically, to iodinated and radioiodinated diacylglycerol analogues.

Diacylglycerols have recently been attracting attention because of their ability to activate protein kinase C (hereinafter PK-C). PK-C is a phosphorylating enzyme which is believed to be involved in signal transduction and tumor promotion by phorbol diesters and related compounds. Phospholipid and calcium are required for activation of the PK-C enzyme. The affinity of PK-C for $Ca^{+2}$ ions is increased by diacylglycerol, which is transiently produced by the action of phospholipase C on phosphatidylinositol 4,5-bisphosphate in response to biological stimuli. The binding of diacylglycerols to PK-C is stoichiometric and competitive with phorbol diesters. Both diacylglycerols and phorbol diesters activate the PK-C enzyme, which, once activated, phosphorylates any of a number of proteins such as histone H1, myelin basic protein, cardiac troponin I and T, and a 40 kilodalton protein in platelets. In this way, diacylglycerol acts as a second messenger in the production of a biological response.

It appears that diacylglycerols and phorbol diesters have differences in their mechanisms of action. A possible explanation for this is that phorbol diesters are not metabolized as readily as diacylglycerols. It is known that phorbol diesters are not substrates for diacylglycerol lipase or diacylglycerol kinase, the enzymes which are primarily responsible for inactivation of diacylglycerols. Elucidation of the differences between these two types of compounds may lead to a greater understanding of the mechanism of tumor promotion by phorbol diesters. Therefore, a biological probe for identification and characterization of PK-C binding sites and mechanisms of action of diacylglycerols would be of great significance to investigators in this field. Moreover, such a probe would enable researchers to ascertain whether synthesized diacylglycerol analogues could be modifiers of the normal biological action of natural occurring diacylglycerols, and thus could have pharmacological effect.

Currently, tritiated phorbol diesters, such as [$^3$H]phorbol dibutyrate, are available for use in studying the mechanism of action of phorbol diesters in tumor promotion. There are currently no radioactive diacylglycerol analogues available for studying the mechanism of action of diacylglycerols. While tritiated compounds are radioemissive, the emission is strictly of the week beta-type. Thus, any interfering structure, such as nearby tissue in vivo, completely absorbs or at least substantially masks the emission before the $^3$H can be detected. Therefore, beta-measuring instruments must be highly sensitive and intervening tissue absorption must be factored-in, thereby increasing the problems created by the use of beta-emissive radio-tagged compounds in laboratory situations. There is therefore a need for radio-tagged compounds for binding to PK-C sites having relatively strong emissive characteristics, as such would be of substantial benefit to investigators of such reactions at the molecular level.

Moreover, PK-C is present in high concentrations in brain tissue and certain tumors, such as leukemia tumors. Since diacylglycerols bind to PK-C, a radioactive form of diacylglycerols would be useful as a non-invasive site-specific imaging agent for organs and tumors where PK-C is concentrated.

Two of the most widely used imaging modalities, radiography and radioisotope scanning, owe much of their success to the development of suitable radiopaques and radiopharmaceuticals. Iodine has played an important role in the development of suitable radiopaque and radiopharmaceutical compounds. Iodine not only imparts the necessary electron density to radiopaques; but can, in its various isotope states (for example, the clinically used isotopes: $I^{123}$, $I^{125}$, and $I^{131}$), emit gamma radiation essential for gamma-camera scintigraphy. Thus, there is a need for iodinated and/or radioiodinated diacylglycerol analogues which are physiologically acceptable and non-toxic for administration to a living being for noninvasive imaging techniques. There is additionally a need for radioactive forms of diacylglycerols for use in tissue distribution studies, and as probes in determining uptake of diacylglycerols into intact cells, in cellular distribution studies, translocation of PK-C from cytosol to membrane upon activation, and biological responses to PK-C activation.

It is, therefore, an object of this invention to provide novel analogues of diacylglycerol, in particular, novel iodinated and radioiodinated analogues of diacylglycerol.

It is another object of this invention to provide novel iodinated and radioiodinated analogues of diacylglycerol as modifiers of PK-C function.

It is also an object of this invention to provide novel iodinated and radioiodinated analogues of diacylglycerol as radiopaques and radiopharmaceuticals.

It is a further object of this invention to provide novel iodinated and radioiodinated analogues of diacylglycerol as radiopaques and radiopharmaceuticals which are physiologically acceptable and non-toxic.

It is additionally an object of this invention to provide novel iodinated analogues of diacylglycerol which will opacify soft tissue when administered in small doses.

It is yet a further object of this invention to provide novel iodinated analogues of diacylglycerol which can be radiotagged for use in scintigraphy.

It is also another object of this invention to provide novel radioiodinated analogues of diacylglycerol which will be cleared from the body of a living being to which it has been administered within a reasonable period of time, while also being sufficiently stable to permit adequate residence time for high-quality imaging.

It is yet an additional object of this invention to provide novel iodinated and radioiodinated diacylglycerol analogues which can be prepared and analyzed more easily than currently available tritiated phorbol diester compounds.

It is still another object of this invention to provide novel iodinated and radioiodinated diacylglycerol analogues which have a higher specific activity than currently available tritiated phorbol diester compounds.

It is a yet further object of this invention to provide novel techniques and methods of making iodinated and radioiodinated diacylglycerol analogues.

It is also a further object of this invention to provide iodinated and radioiodinated diacylglycerol analogues as tracers for monitoring the interaction of such analogues with PK-C both in vitro and in vivo for characterizing the binding site and its role in cell proliferation.

SUMMARY OF THE INVENTION

The foregoing and other objects are achieved by this invention which provides a novel iodinated arylaliphatic 1,2-diacylglycerol compound of the general formula:

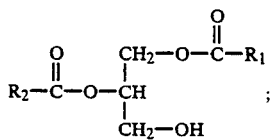

wherein $R_1$ and $R_2$ are selected form the group consisting of (1) an amino-substituted-2,4,6-triiodophenyl of the general formula:

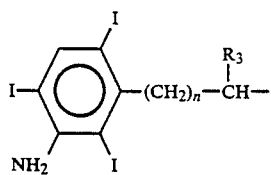

wherein $R_3$ is selected from the group of H and lower alkyls, and n is an integer from 1 to 10; (2) a monoiodophenyl of the general formula:

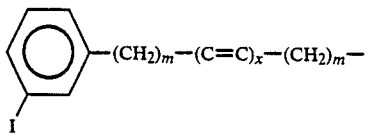

wherein m is an integer from 1 to 10, x is an integer from 0, to 5; and (3) saturated and unsaturated aliphatic hydrocarbon chains having 1 to 25 carbon atoms; wherein only one of $R_1$ and $R_2$ has at least one iodine atom.

In a specific illustrative embodiment of the invention, I is selected from the group of stable and radioactive isotopes of iodine. The radioactive isotopes may include the group of $^{122}I$, $^{123}I$, $^{125}I$, and $^{131}I$.

In accordance with a method aspect of the invention, a physiologically effective amount of the inventive compound is administered to the body of a living being.

As will be described in detail hereinbelow, some of the compounds of the present invention are:
1-iopanoyl-2-palmitoyl-rac-glycerol;
1-[15-(m-iodophenyl)pentadecanoyl]-2-acetyl-rac-glycerol;
1-palmitoyl-2-desethyliopanoyl-rac-glycerol;
1-octanoyl-2-[3-(m-iodophenyl)propanoyl]-rac-glycerol;
1-acetyl-2-[15-(m-iodophenyl)-pentadecanoyl]-rac-glycerol;
and
1-palmitoyl-2-iopanoyl-rac-glycerol.

In accordance with an inventive use aspect of the invention, the compound having the aforementioned general formula is utilized as a site-specific radioactive tracer compound. In an illustrative embodiment, I is selected from the group of $^{122}I$, $^{123}$, $^{125}I$, and $^{131}I$. An effective amount of the radioactive tracer compound is administered to the body of the living being.

In addition to the foregoing, the compound having the aforementioned general formula is used as a radioactive binder assay compound for PK-C sites. In this aspect of the invention, the compound has a radioactive iodine atom, which in certain embodiments is $^{125}I$.

BRIEF DESCRIPTION OF THE DRAWINGS

Comprehension of the invention is facilitated by reading the following detailed description in conjunction with the annexed drawing, in which:

FIG. 2 is a flow chart of a scheme for synthesis of a 1,2-substituted diacylglycerol compound, specifically 1-palmitoyl-2-desethyliopanoyl-rac-glycerol;

FIG. 4 is a flow chart of a scheme for synthesis of a 1,2-substituted dibutyrate; diacylglycerol compound, specifically 1-octanoyl-2-[3-(m-iodophenyl)propanoyl]-rac-glycerol;

FIG. 7 is a graphical plot which illustrates competitive binding of 1-palmitoyl-2-iopanyl-rac-glycerol (PIG),1-iopanoyl-2-palmixoyl-rac-glycerol and 1-oleoyl-2-acetyl-rac-glycerol (OAG) as a percent of the control level of [$^3$H]phorbol dibutyrate;

FIG. 8 is a graphical plot which illustrates competitive binding of 1-acetyl-2-[15-(m-iodophenyl)pentadecanoyl]-rac-glycerol (AC-IPPG) and 1-oleoyl-2-acetyl-rac-glycerol as a percent of the control level of [$^3$H]phorbol dibutyrate.

DETAILED DESCRIPTION

The novel iodinated and radioiodinated compounds of the invention herein have the general formula of a 1,2-disubstituted diacylglycerol:

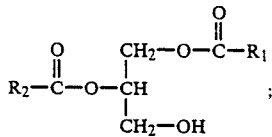

In one embodiment of the invention, the 1-position ($R_1$) is an amino-substituted -2,4,6-triiodophenyl of the general formula:

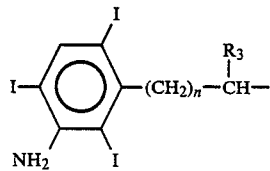

wherein $R_3$ is H or a lower alkyl, and n is an integer from 1 to 10 and $R_2$ is a or chain saturated or unsaturated aliphatic hydrocarbon chain having 1 to 25 carbon atoms. In yet another embodiment, the aforementioned $R_1$ and $R_2$ moieties are reversed so that the iodinated side chain is at the 2-position.

In another preferred embodiment, $R_1$ is a monoiodophenyl aliphatic chain of the general formula:

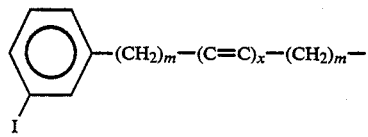

wherein m is an integer from 1 to 10, x is an integer from 0 to 5 and $R_2$ is a or saturated or unsaturated aliphatic hydrocarbon chain having 1 to 25 carbon atoms. In yet another alternative embodiment, the monoiodophenyl aliphatic chain may occur at the 2-position.

The following examples of specific embodiments of the invention are also illustrative of methods for synthesizing the iodinated and radioiodinated diacylglycerol analogues of the instant invention:

EXAMPLE 1

3-Amino-α-ethyl-2,4,6-triiodobenzenepropanoic acid, also known as iopanoic acid, is an example of an example of a amino-substituted triiodophenyl aliphatic side chain of the type preferred for substituting at the 1- or 2-positions in the diacylglycerol analogues of the instant invention.

Figure 1:
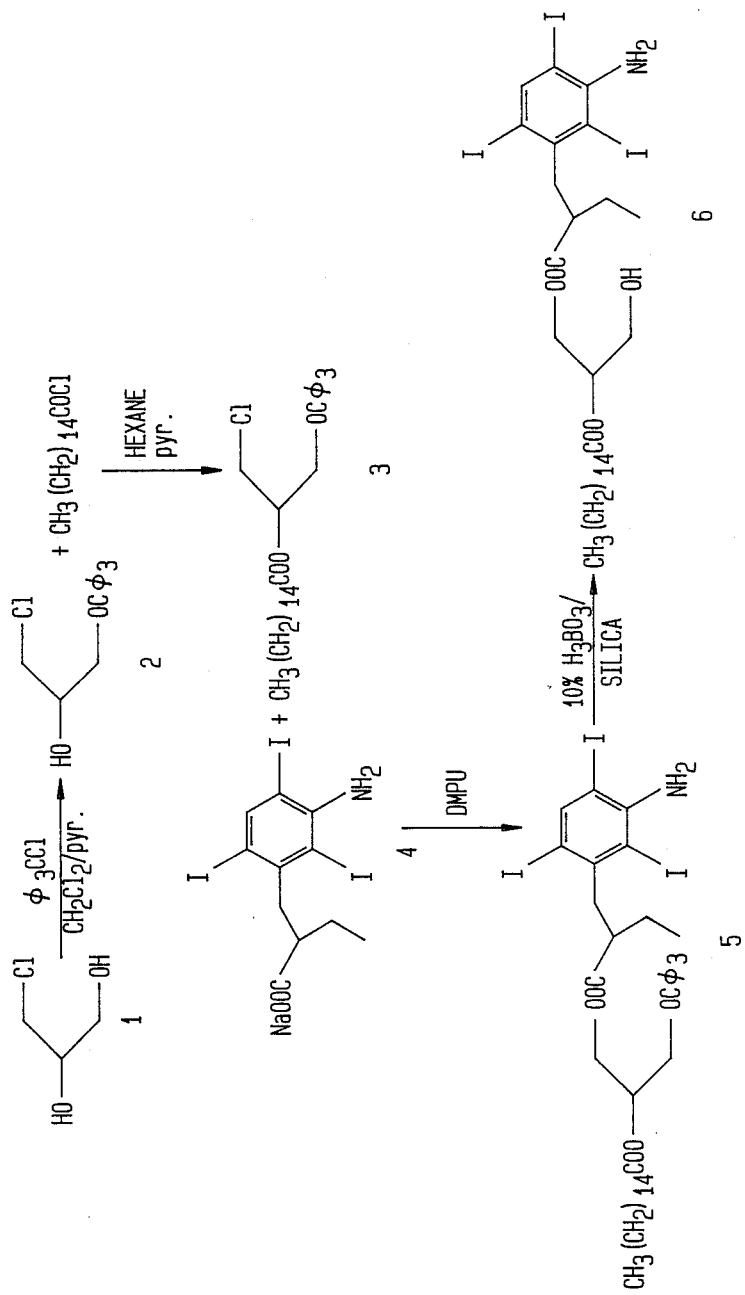
FIG. 1 is a flow chart of a scheme for synthesis of a 1,2-substituted diacylglycerol compound, specifically 1-iopanoyl-2-palmitoyl-rac-glycerol.

FIG. 1 shows an illustrative preparatory scheme for 1-iopanoyl-2-palmitoyl-rac-glycerol which will be described in detail in this example.

3-Chloro-1,2-rac-propanediol (5.00 g, 45.23 mmol), compound 1, was combined with trityl chloride (Ph$_3$CCl; 8.41 g, 30.17 mmol) and dry pyridine (pyr.; 28 ml) in a flame-dried round bottom flask and stirred at room temperature for two days. The reaction mixture was diluted with toluene (120 ml), and washed as follows: twice with cold water, three times with 1 N HCl, once with saturated NaHCO$_3$ and once with brine. The organic phase was dried with MgSO$_4$ and the toluene solvent was evaporated to produce crude product, compound 2, 1-O-Trityl-3-chloro-1,2-rac-propanediol (10.95 g, 69% yield).

1-O-Trityl-3-chloro-1,2-rac-propanediol (2.00 g, 5.67 mmol) was placed in a 50 ml round bottom flask that had been flame dried under nitrogen. Pyridine (0.59 ml, 7.37 mmol) and dry hexane (15 ml) were added to the flask. A solution of palmitoyl chloride, CH$_3$(CH$_2$)$_{14}$COCl (1.87 g, 6.80 mmol) in hexane (5 ml) was added to the flask dropwise. Eventually compound 2 went into solution and a white solid formed. The mixture was stirred at room temperature for two hours and then heated at reflux for 4.5 hours. The mixture was then cooled and water was added. The organic layer was washed as follows: once with 0.5 M NH$_4$OH in methanol:water (3:1) and twice with methanol:water (3:1). The organic layer was dried with MgSO$_4$ and evaporated. The resulting product was purified to the extent possible by column chromatography on 125 g silica gel with hexanes:ethyl acetate (10:1) solvent. The resulting product is shown on FIG. 1 as compound 3, 1-O-trityl-2-palmitoyl-3-chloro-1,2-rac-propanediol (3.24 g oil, 97% yield).

Iopanoic acid (2.50 g, 4.38 mmol) was dissolved in diethyl ether (75 ml). Concentrated aqueous NaOH (0.42 ml) was added to the iopanoic acid solution and the mixture was left to chill in the refrigerator overnight. Additional NaOH (10 drops) was added to precipitate solid and the reaction mixture was left to cool for another day. The salt was then removed by filtration and washed with ether. Recrystallization from water produced a white crystalline product which was sodium iopanoate, compound 4 (2.49 g, 96% yield).

Sodium iopanoate (300 mg, 0.51 mmol) was placed in a flame-dried flask. Compound 3, 1-O-trityl-2-palmitoyl-3-chloro-1,2-rac-propanediol, was dissolved in dimethylpropylene urea (DMPU; 8 ml) and added to the flask. The mixture was heated at 135°-140° C. for two hours and allowed to cool. Petroleum ether was added to dilute the cooled mixture. The organic layer was washed: three times with water and three times with 0.5 M NH$_4$OH in methanol:water (3:1). The organic layer was then dried with MgSO$_4$ and evaporated. Column chromatography on 100 g silica gel with hexanes:ethyl acetate (15:1) solvent was used to purify the product, compound 5, 1-iopanoyl-2-palmitoyl-3-O-trityl-rac-glycerol (620 mg, 37% yield).

A column was prepared with 10% boric acid in silica gel (3.5 g) using petroleum ether as the solvent to detritylate compound 5. The tritylated compound 5 was adsorbed to 0.4 g silica gel and added to the top of the column. The column was eluted with petroleum ether (400 ml), petroleum ether:ether (95:5) (300 ml) and petroleum ether:ether 3:1 (350 ml). The fractions containing product were evaporated, then the residue was dissolved in CHCl$_3$, washed four times with water, dried with MgSO$_4$, and evaporated to produce compound 6, 1-iopanoyl-palmitoyl-rac-glycerol (154.9 mg, 60% yield).

EXAMPLE 2

Example 2 is an alternative embodiment wherein an amino-substituted-2,4,6-triiodophenyl aliphatic side chain is linked to the 2-position on the diacylglycerol backbone structure. Referring to FIG. 2, an illustrative preparatory scheme for 1-palmitoyl-2-desethliopanoyl-rac-glycerol is shown.

Isopropylidene glycerol, compound 20, is the starting point for this reaction sequence. Isopropylidene glycerol (17.4 ml, 140.0 mmol), pyridine (10.8 ml, 135.2 mmol) and CHCl$_3$ (200 ml) were combined and the reaction mixture was cooled to a temperature of 0° C. Palmitoyl chloride (32.0 g, 116.4 mmol) was dissolved in CHCl$_3$ (100 ml) and added dropwise to the reaction mixture. The reaction mixture was stirred overnight and the solvent was evaporated. Ether was added to precipitate the pyridine hydrochloride, which was removed by filtration. The filtrate was washed four times with H$_2$O. The organic layer was dried over MgSO$_4$ and evaporated. The crude product, compound 21, 1-palmitoyl-2,3-isopropylidene-rac-glycerol, was used in the next step without further purification.

1-Palmitoyl-2,3-isopropylidene-rac-glycerol (10 g, 27 mmol) was placed in a round bottom flask with boric acid (8.36 g, 135.1 mmol) and trimethyl borate [$(CH_3O)_3B$; 50 ml]. The flask was fitted with a reflux condenser and the mixture was heated to 100° C. for 10 minutes. The reflux condenser was exchanged for a distillation condenser and the mixture was placed under vacuum and heated for 15 minutes. The residue was cooled and dissolved in either and $H_2O$. The aqueous and organic phases were separated and the organic layer was washed three times with water, dried over $MgSO_4$, and evaporated. The residue was recrystallized in hexanes:ethyl ether (3:2) volume ratio to yield 1-palmitoyl-rac-glycerol, compound 22.

1-Palmitoyl-rac-glycerol (6.0 g, 18.2 mmol) and 4-dimethylaminopyridine (DMAP) were placed in a flame-dried round bottom flask and $CH_2Cl_2$ (120 ml) and triethylamine (5.1 ml, 36.6 mmol) were added to the flask. The mixture was stirred until most of the solid had dissolved and then trityl chloride (5.58 g, 20.0 mmol) was added. This mixture was stirred overnight at room temperature and then poured into ice water. The organic and aqueous phases were separated. The aqueous phase was washed with $CH_2Cl_2$. The organic phase was washed three times with 0.5 N NHCl and twice with water. The organic phase was then dried with $MgSO_4$ and evaporated. Chromatography (120 g silica gel, hexanes:ethyl acetate (4:1) solvent) and recrystallization in petroleum ether yielded pure product, compound 23, 1-palmitoyl-3O-trityl-rac-glycerol (8.26 g, 79% yield).

Desethyliopanoic acid (4.00 g, 7.37 mmol), 1-palmitoyl-3-O-trityl-rac-glycerol (4.22 g, 7.37 mmol) and DMAP were combined in a flame-dried flask and $CH_2Cl_2$ (70 ml) was added. Dicyclohexylcarbodiimide (DCC; 1.53 g, 7.39 mmol) was added and the mixture was stirred overnight at room temperature. The reaction mixture was extracted twice with saturated $NaHCO_3$, once with water, and once with brine. The organic phase was dried with $MgSO_4$ and evaporated. Chromatography (180 g silica gel, hexanes:ethyl acetate (7:1) solvent) resulted in pure compound 24, 1-palmitoyl-2-desethyliopanoyl-3-O-trityl-rac-glycerol (6.22 g, 77% yield).

1-Palmitoyl-2-desethyliopanoyl-3-O-trityl-rac-glycerol (1.50 g, 1.37 mmol) was adsorbed to 10% $H_3BO_3$/silica gel (2.00 g) and placed on top of a column of 10% $H_3BO_3$/silica gel (15.00 g). The column was eluted with petroleum ether (850 ml), petroleum ether:ether 95:5 (200 ml) and petroleum ether:ether 3:2 (400 ml . The last fraction eluted from the column was evaporated, dissolved in $CHCl_3$, washed four times with water, dried with $MgSO_4$ and evaporated. The resulting product was pure compound 25, 1-palmitoyl-2-desethyliopanoyl-rac-glycerol (0.83 g, 71% yield).

EXAMPLE 3

Figure 3:
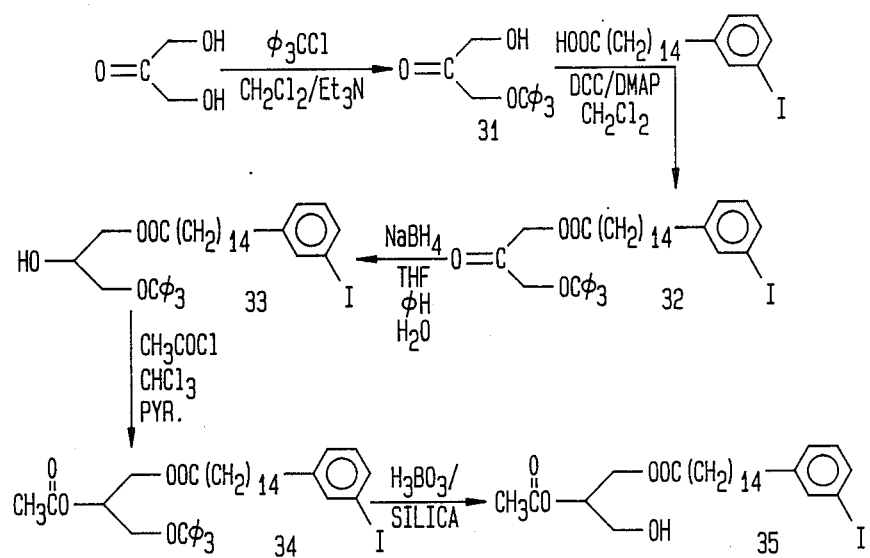
FIG. 3 is a flow chart of a scheme for synthesis of a 1,2-substituted diacylglycerol compound, specifically 1-[15-(m-iodophenyl)pentadecanoyl]-2-acetyl-rac-glycerol.

Example 3 is directed to an embodiment of the invention wherein a monoiodophenylaliphatic chain is substituted on the 1-position of the diacylglycerol backbone structure. In this particular illustrative embodiment, 1-[15-(m-iodophenyl)pentadecanoyl]-2-acetyl-rac-glycerol is prepared in accordance with the scheme shown on FIG. 3.

1,3-Dihydroxy-2-propanone dimer (3.00 g, 16.65 mmol) and DMAP were placed in a flame-dried round bottom flask. $CH_2Cl_2$ (83 ml) and triethylamine (4.9 ml, 35.0 mmol) were added to the flask. Trityl chloride (9.28 g, 33.30 mmol) was dissolved in $CH_2Cl_2$ (35 ml) and added slowly to the reaction mixture. The entire mixture was stirred overnight at room temperature. The mixture was poured into ice water and the aqueous and organic phases were separated. The $CH_2Cl_2$ layer was washed twice with 1 N HCl and once with brine. The organic layer was then dried with $MgSO_4$ and evaporated. The product was chromatographed in two batches (130 g silica gel each, and hexane:ethyl acetate (10:1) solvent) to purify ketone compound 31, 3-O-trityl-13-dihydroxy-2-propanone (1.89 g; 17% yield).

3-O-Trityl-1,3-dihydroxy-2-propanone (0.38 g. 1.14 mmol), 15-(m-iodophenyl)pentadecanoic acid (0.51 g, 1.14 mmol) and DMAP were dissolved in $CH_2Cl_2$ (10.7 ml). DCC (0.26 g, 1.25 mmol) was added and the reaction mixture was stirred overnight at room temperature. The reaction mixture was then diluted with $CH_2Cl_2$ and the organic layer was washed as follows: twice with 1 N HCl, once with saturated $NaHCO_3$, once with brine and once with water. The organic layer was then dried over $MgSO_4$ and evaporated. Column chromatography with 100 g silica gel and a hexane:ethyl acetate (12:1) solvent resulted in purification of compound 32, 1-[15-(m-iodophenyl)pentadecanoyl]-3-O-trityl-1,3-dihydroxy-2-propanone (0.61 g, 70% yield).

1-[15-(m-Iodophenyl)pentadecanoyl]-3-O-trityl-1,3-dihydroxy-2-propanone (0.52 g, 0.69 mmol) was placed in a round bottom flask, followed by tetrahydrofuran (THF; 6 ml), benzene (2 ml) and $H_2O$ (0.4 ml). The mixture was cooled to 5° C. before sodium borohydride ($NaBH_4$; 42.5 mg, 1.12 mmol) was added. This mixture was stirred for 30 minutes. Acetic acid (23 μl) was added to destroy excess $NaBH_4$ and the mixture was diluted with $CH_2Cl_2$. The organic layer was extracted with saturated $NH_4Cl$ twice, water once, and brine once. The organic layer was dried with $MgSO_4$ and evaporated. Column chromatography on 50 g silica gel and a hexane:ethyl acetate (8:1) solvent resulted in purification of a pure alcohol, compound 33, 1-[15-(m-iodophenyl)pentadecanoyl[-3-O-trityl-rac-glycerol (0.40 g, 77%).

1-[15-(m-Iodophenyl)pentadecanoyl]-3-O-trityl-rac-glycerol (0.34 g, 0.45 mmol) was dissolved in ethanol free $CHCl_3$ (2.2 ml) in a two-necked flask. Pyridine (0.06 ml, 0.79 mmol) was added, followed by acetyl chloride (0.09 ml, 1.26 mmol). The reaction mixture was stirred for 7 hours, then $H_2O$ was added to destroy the excess acetyl chloride. This mixture was diluted with $CHCl_3$, washed twice with 1 N HCl and once with brine. The organic layer was dried over $MgSO_4$ and the solvent was evaporated. Chromatographic purification yielded pure compound 34, 1-[15-(m-iodophenyl)pentadecanoyl]-2-acetyl-3-O-trityl-rac-glycerol. (0.31 g, 86% yield).

1-[15-(m-Iodophenyl)pentadecanoyl]-2-acetyl-3-O-trityl-rac-glycerol (251.7 mg, 0.31 mmol) was adsorbed to 10% $H_3BO_3$/silica gel (0.3 g) and placed on a column of 10% $H_3BO_3$/silica gel (2.6 g). The column was eluted with petroleum ether (200 ml), pet. ether:ether 95:5 (125 ml), and pet. ether:ether 3:1 (500 ml). The end product, compound 35, was eluted in the last fraction. Compound 35 is 1-[15-(m-iodophenyl)pentadecanoyl]-2-acetyl-rac-glycerol (31.8 mg, 18% yield).

EXAMPLE 4

In this alternative embodiment of the invention, the monoiodophenyl aliphatic side chain is substituted at the 2-position on the diacylglycerol backbone. Reference to FIG. 4 shows an illustrative preparatory scheme for 1-octanoyl-2-[3-(m-iodophenyl)propanoyl]-rac-glycerol.

Isopropylidene glycerol (10.95 g, 82.84 mmol) was placed in a flame-dried flask with $CH_2Cl_2$ (225 ml). Pyridine (10.54 ml, 131.57 mmol) was added to the flask, followed by octanoyl chloride, $ClCO(CH_2)_6CH_3$, (18.42 g, 113.24 mmol) in $CH_2Cl_2$ This mixture was stirred overnight and then poured into ice water. The phases were separated and the organic phase was extracted twice with 1 N HCl and once with brine. The organic layer was dried over $MgSO_4$ and evaporated. The crude product, compound 41, 1-octanoyl-2,3-isopropylidene-rac-glycerol, was used without further purification.

1-Octanoyl-2,3-isopropylidene-rac-glycerol (26.04 g, 100.8 mmol), boric acid (31.19 g, 504.45 mmol) and trimethyl borate (185 ml) were combined in a round bottom flask. The mixture was heated to 90° C. for 10 minutes then a reflux condenser which was exchanged for a distillation condenser prior to putting the system under vacuum and heating for an additional 15 minutes. The residue was dissolved in ether and water and the resultant phases were separated. The organic phase was washed three times with water, dried with $MgSO_4$, and evaporated. The solid product was recrystallized from petroleum ether:ether (3:1) to produce white crystals of compound 42, 1-octanoyl-rac-glycerol (11.33 g, 63% yield from isopropylidene glycerol).

1-Octanoyl-rac-glycerol (10.00 g, 45.81 mmol) and DMAP were placed in a flame-dried round bottom flask, followed by triethylamine (13.0 ml, 93.27 mmol) and $CH_2Cl_2$ (200 ml). When the solid dissolved, trityl chloride (14.07 g, 50.47 mmol) was added and the mixture was stirred at room temperature for two days. The mixture was poured into ice water and the two phases were separated. The organic layer was washed three times with 1 N HCL and twice with water, dried over $MgSO_4$, and evaporated. The product was purified by chromatography in two batches, (150 g silica gel each with hexanes:ethyl acetate (8:1) solvent) to yield compound 43, 1-octanoyl-3-O-trityl-rac-glycerol (9.96 g, 47% yield).

1-Octanoyl-3-O-trityl-rac-glycerol (414 mg, 0.90 mmol), 3-(m-iodophenyl)propanoic acid (250 mg, 0.91 mmol) and DMAP were dissolved in $CH_2Cl_2$ (8.3 ml). DCC (206 mg, 1.00 mmol) was added and the mixture was stirred overnight. The mixture was then diluted with $CH_2Cl_2$. The organic and aqueous phases were separated and washed twice with 1 N HCl, once with saturated $NaHCO_3$, once with $H_2O$, and once with brine. The organic layer was then dried over $MgSO_4$ and evaporated. Purification by chromatography on 12 g silica gel and with a hexanes:ethyl acetate (8:1) solvent yielded pure compound 44, 1-octanoyl-2-[3-(m-iodophenyl)propanoyl]-3-O-trityl-rac-glycerol (473.5 mg. 73% Yield).

1-Octanoyl-2-[3-(m-iodophenyl)propanoyl]-3-O-trityl-rac-glycerol (373.6 mg, 0.52 mmol) was adsorbed to 10% boric/silica gel (400 mg) and placed on a column of boric acid/silica (4 g). The column was eluted with petroleum ether:ether 3:1 (200 ml). The last eluent contained pure diacylglycerol compound 45, 1-octanoyl-2-[3-(m-iodophenyl)propanoyl]-rac-glycerol (218.1 mg, 88% yield).

Radioiodination of the Diacylglycerol Analogues

For certain uses, such as scintigraphy or experimental evaluation of tissue distribution, it is desirable to create radioactive compounds. Radioiodination of the iodinated diacylglycerol analogues disclosed herein, or one of the intermediates in the synthesis pathway, such as a trityl-protected compound, can be accomplished by a variety of techniques, some of which are known in the art. For example, aromatic compounds with electron donating groups (such as anilines) can be radiolabelled by electrophilic iodination in the presence of radioiodine, iodine monochloride, chloramine-T, iodogen, etc. Unactivated aromatic rings, can be radioiodinated by exchange of a leaving group, such as aryl boronic acids, aryl thallium trifluoroacetates, triazenes or metallated arenes with radioiodine. Direct electrophilic radioiodination of a phenyl ring is yet another alternative, but may require the use of isomeric mixtures which are difficult to separate. Iodine exchange of aryl iodides with radioiodine may be a preferable approach insofar as no complex separation techniques are necessary since the substrate and radioiodinated product are chemically identical.

In a preferred embodiment of the invention, an isotopes exchange-type technique is utilized wherein the substrate and radioiodine are reacted at an elevated temperature in a "melt." The molten reaction medium possesses a sufficiently high dielectric constant to solubilize both the substrate and radioiodide. Examples of reaction media currently in use are benzoic acid (mp 122° C., bp 249° C.) and acetamide (mp 82° C., bp 221° C.). In a specific preferred embodiment, an acidic exchange medium comprising pivalic acid, a homolog of acetic acid, also known as trimethyl acetic acid, was used. Pivalic acid has a melting point of 33° C. and a boiling point of 164° C. The exchange reaction was essentially complete in about 1 hour at 155° C.

Of course, any isotope of iodine such as the clinically used isotopes, $I^{122}$, $I^{123}$, $I^{125}$ and $I^{131}$ can be used. $I^{125}$ is preferred for in vitro work in the laboratory due to its relatively long half-life. For radiodiagnostic purposes in humans, $I^{123}$ or $I^{131}$ is preferred due to their shorter half-lives. The advent of positron emission tomography has also created a use for the positron-emitting $I^{122}$ isotope. The radioiodination procedures may be modified, as known by those of skill in the art, to compensate for the difference in half-life.

The above-described iodinated or radioiodinated diacylglycerol analogues may be solubilized in a suitable transport agent, or carrier vehicle, and administered to mammalian subjects as radiologic agents by any known manner, preferably intraparentrally such as intravenously or intraperitonally. Moreover, site-specific delivery of compounds containing certain isotopes of iodine can be administered for its therapeutic effects in damaging tumor cells. Of course, the novel 1,2-diacylglycerol compounds of the present invention can be provided as salts thereof, having a form such as hydrochloride, tartrate, citrate, bromide, chloride, or sulfate.

Competitive Binding Studies

The ability of 1,2-diacylglycerol analogues disclosed herein to bind with PK-C in vitro was examined by competitive binding studies.

Lyzed Cells

A binding assay was devised wherein crude rat brain cytosol was the source of PK-C enzyme. The reaction was carried out in plastic centrifuge tubes. The total solution volume was 250 μl and comprised: phosphatidylserine (100 μg/ml), calcium chloride (10 mM), bovine gamma globulin (5 mg/ml), tris-HCl (50 mM), crude rat brain preparation (200 μg/ml), and the desired concentration of diacylglycerol, which had been sonicated with phosphatidylserine. The tubes were incubated at 37° C. for 30 minutes. The protein was then precipitated by addition of 187 μl of 35% polyethylene glycol and removed by centrifugation for 4 minutes. The supernatant was removed and the pellet rinsed with tris/polyethylene glycol, dried, cut and counted.

The results are described hereinbelow and referenced to FIGS. 5 to 8, which are graphic representations illustrating competitive binding of[$^3$H]PDBu and 1,2-diacylglycerol in accordance with the invention in comparison with a naturally occurring diacylglycerol, 1-oleoyl-acetyl-rac-glycerol. The graphs of FIGS. 5 and 6 are expressed in terms of the log of inhibitor concentration in moles (M) versus specific binding in counts per minute (cpm).

Figure 5:
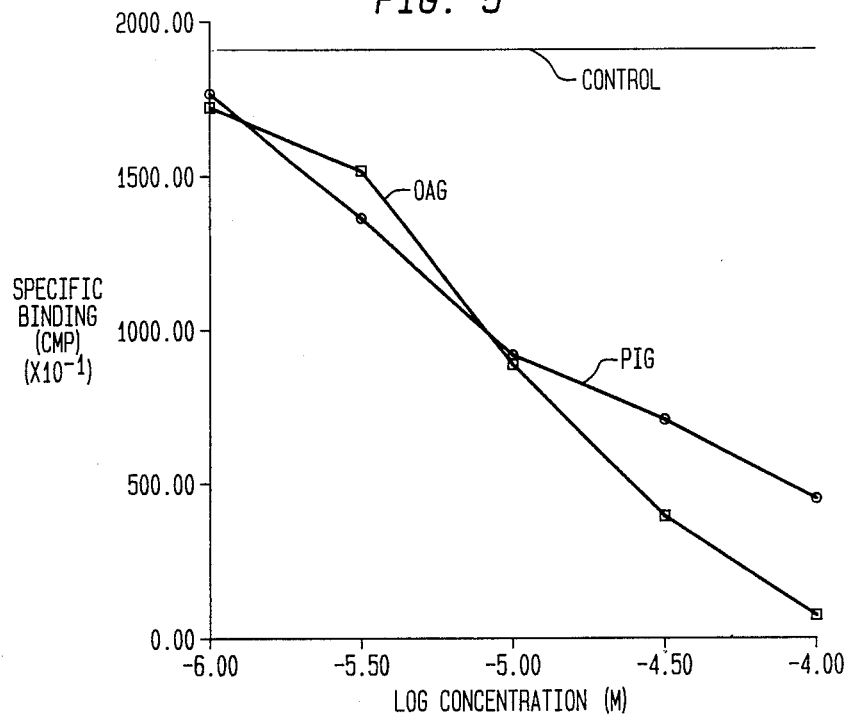
FIG. 5 is a graphical plot which illustrates competitive binding of 1-palmitoyl-2-iopanyl-rac-glycerol (PIG) and 1-oleoyl-2-acetyl-rac-glycerol (OAG) with [$^3$H]phorbol
Figure 6:
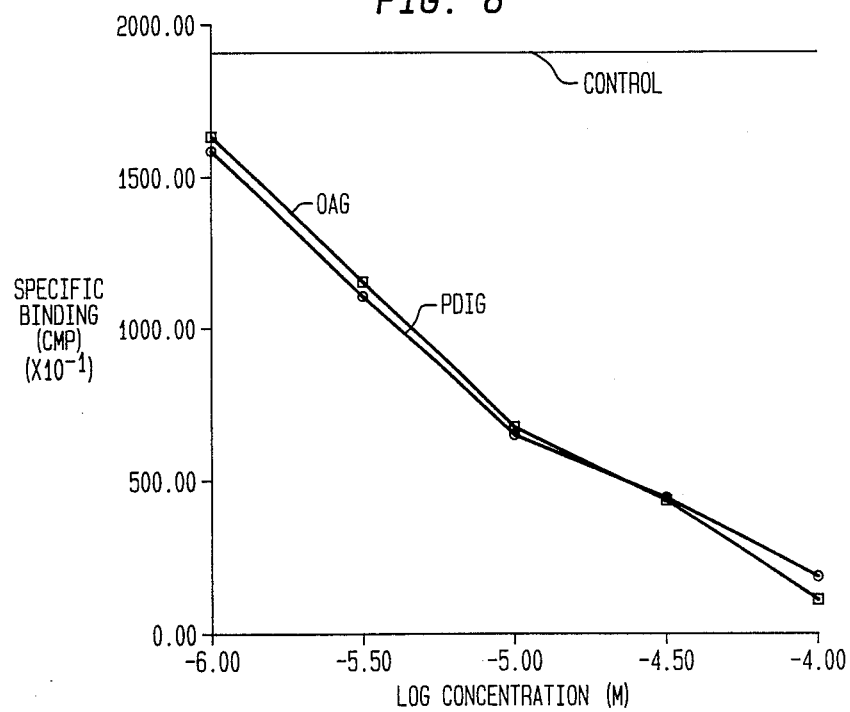
FIG. 6 is a graphical plot which illustrates competitive binding of 1-palmitoyl-2-desethyliopanoyl-rac-glycerol (PDIG) and 1-oleoyl-2-acetyl-rac-glycerol (OAG), with [$^3$H]phorbol dibutyrate.

FIG. 5 illustrates competitive binding of 1-palmitoyl-2-iopanyl-rac-glycerol (PIG) and 1-oleoyl-2-acetyl-rac-glycerol (OAG) with [$^3$H]phorbol dibutyrate. The specific binding of 100% [$^3$H]phorbol dibutyrate is shown as a solid line FIG. 6 illustrates competitive binding of 1-palmitoyl-2-desethyliopanoyl-rac-glycerol and 1-oleoyl-2-acetyl-rac-glycerol, with [3H]phorbol dibutyrate.

FIGS. 7 and 8 are expressed in terms of the log of inhibitor concentration in moles (M) versus specific binding of the 1,2-diacylglycerol expressed as a percent of control binding.

FIG. 7 illustrates competitive binding of 1-palmitoyl-2-iopanyl-race-glycerol (PIG),1-iopanoyl-2-palmitoyl-rac-glycerol(IPG) and 1-oleoyl-2-acetyl-rac-glycerol (OAG) as a percent of the control level of [$^3$H]phorbol dibutyrate.

FIG. 8 illustrates competitive binding of 1-acetyl-2-[15-(m-iodophenyl)pentadecanoyl]-rac-glycerol (AC-IPPG) and 1-oleoyl-2-acetyl-rac-glycerol as a percent of the control level of the control level of [$^3$H]phorobol dibutyrate.

Intact Cells

The ability of diacylglycerol analogues to enter intact cells and bind with the intracellular PK-C was demonstrated by the following study of [$^3$H]PDBu binding to intact HL-60 cells:

The diacylglycerol composition under investigation was stored in chloroform at −20° C. Prior to use, the diacylglycerol was dried under nitrogen and sonicated in RPMI-1640 growth media. HL-60 cells, derived from a human leukemia cell line, were cultured in RPMI-1640 growth media containing 10% horse serum. The cells were placed in fresh serum-containing growth media 24 hours prior to the experiment. Then, cells in log phase growth were placed in normal serum containing growth media with 20 mM HEPES buffer (pH 7.4) at a concentration of 5×10$^6$ cells/ml. The cells were incubated at 37° C. in 5% CO$_2$/air in the presence of [$^3$H]PDBu and various concentrations of diacylglycerol.

Binding reactions were stopped after 30 minutes by filtering the cells over Whatman glass fiber GF/C filters and rinsing with cold phosphate buffered saline (pH 7.4). The filters were then dried and counted with a scintillation counter. Nonspecific binding was determined by adding 2 μM non-tritiated phorbol diester to parallel binding reactions. Specific [$^3$H]PDBu binding was calculated by subtracting nonspecific [$^3$H]PDBu from the total. All binding data are expressed in terms of specific binding. Specific binding typically represented 80% of the total.

Figure 9:
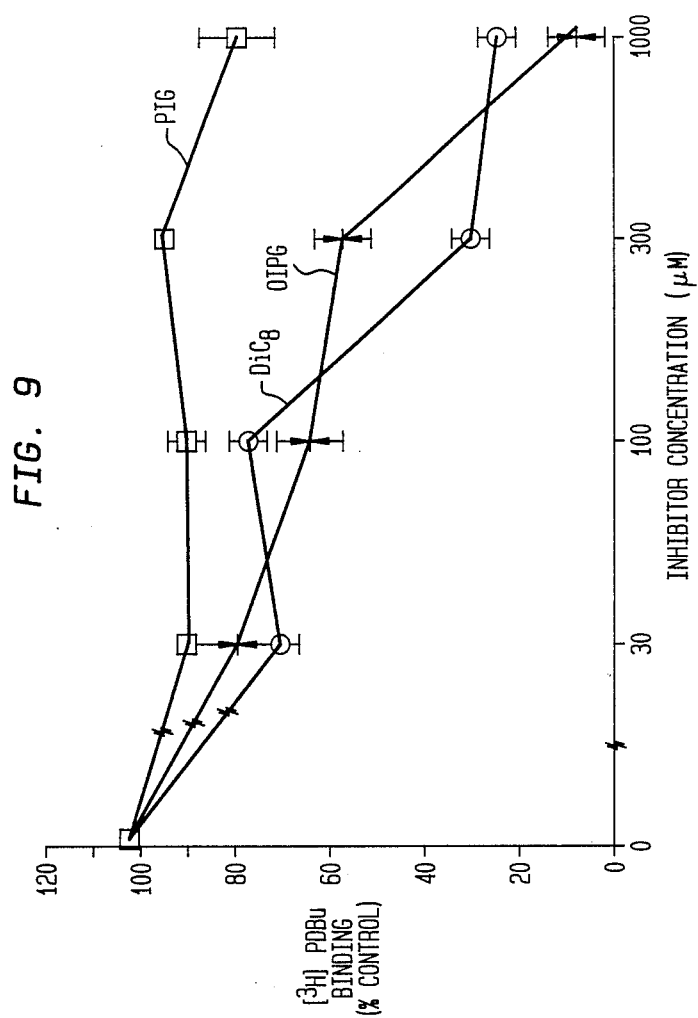
FIG. 9 is a graphical plot which illustrates diacylglycerol inhibition of [$^3$H]PDBu binding in intact HL-60 cells.

FIG. 9 shows a graph of diacylglycerol inhibition of [$^3$H]PDBu binding in intact HL-60 cells expressed as percent [$^3$H]PDBu binding versus inhibitor concentration. The line identified as OIPG represents the data for diacylglycerol produced in Example 4, 1-octanoyl-2-[3-(m-iodophenyl)propanoyl]-rac-glycerol (OIPG). The line identified as DiC$_8$ represents the data for a naturally occurring diacylglycerol, diocantoyl diacylglycerol, which is commercially available from Sigma, St. Louis, MO. For comparative purposes, the line identified as PIG represents data from 1-palmitoyl-2-iopanoyl-rac-glycerol (PIG). This figure clearly shows that 1-octanoyl-2-[3 (m-iodophenyl)propanoyl]-rac-glycerol is capable of entering intact cells and binding to intracellular PK-C in a manner similar to a naturally occurring diacylglycerol.

Although the invention has been described in terms of specific embodiments and applications, persons skilled in this art can, in light of this teaching, generate additional embodiments without exceeding the scope or departing from the spirit of the claimed invention. In particular, the methods of synthesis are merely illustrative and can be modified by those of skill in the art for the production of various substituted diacylglycerol analogues in accordance with the invention. Moreover, other techniques of radio-tagging the analogues may be employed. Accordingly, it is to be understood that the drawings and descriptions in this disclosure are proffered to facilitate the comprehension of the invention and should not be construed to limit the scope thereof.

What is claimed is:

1. A site-specific radioactive tracer compound having the general formula:

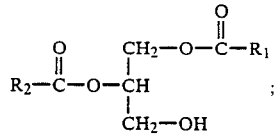

wherein R$_1$ and R$_2$ are selected from the group consisting of (1) an amino-substituted-2,4,6-triiodophenyl of the general formula:

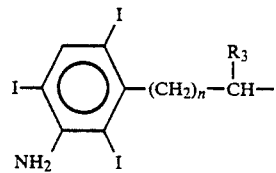

wherein R$_3$ is selected from the group of H and lower alkyls, and n is an integer from 1 to 10; (2) a monoiodophenyl of the general formula:

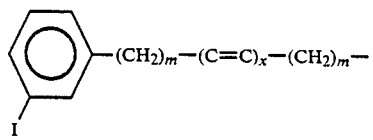

wherein m is an integer from 1 to 10 x is an integer from 0 to 5; and (3(saturated aliphatic hydrocarbon chains having 1 to 25 carbon atoms; wherein only one of $R_1$ and $R_2$ has at least one radioactive iodine atom.

2. The compound of claim 1 wherein I is selected from the group of $^{122}I$, $^{123}I$, $^{125}I$, and $^{131}I$.

3. A method of radioimaging a host comprising the steps of administering of the body of said host an effective amount of a radioactive tracer compound as claimed in claim 1 and subsequently scanning said host.

4. A radioactive binder assay compound for PK-C sites, said compound comprising the general formula:

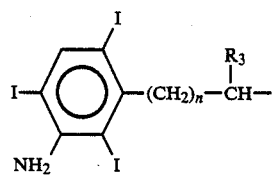

wherein $R_1$ and $R_2$ are selected from the group consisting of (1) an amino-substituted-2,4,6-triiodophenyl of the general formula:

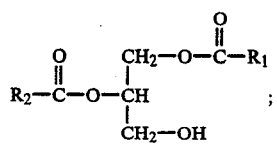

wherein $R_3$ is selected from the group of H and lower alkyls, and n is an integer from 1 to 10; (2a monoiodophenyl of the general formula:

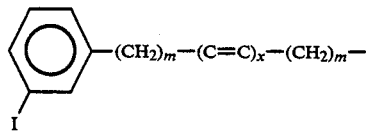

wherein m is an integer from 1 to 10, x is an integer from 0 to 5; and (3) saturated and unsaturated aliphatic hydrocarbon chains having 1 to 25 carbon atoms; wherein only one of $R_1$ and $R_2$ has at least one radioactive iodine atom.

5. The compound of claim wherein I is $^{125}I$.

6. A compound of the general formula:

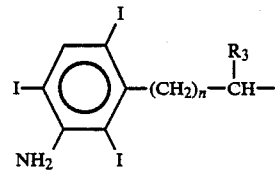

wherein $R_1$ and $R_2$ are selected from the group consisting of (1) an amino-substituted-2,4,6-triiodophenyl of the general formula:

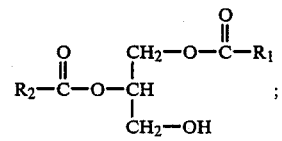

wherein $R_3$ is selected from the group of H and lower alkyls, and n is an integer from 1 to 10; (2) a monoiodophenyl of the general formula:

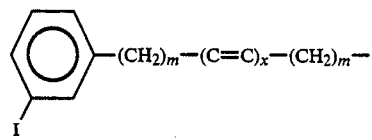

wherein m is an integer from 1 to 10, x is an integer from 0 to 5; and (3) saturated and unsaturated aliphatic hydrocarbon chains having from 1 to 25 carbon atoms; wherein only one of $R_1$ and $R_2$ has at least one radioactive isotope of iodine.

7. The compound of claim 6 wherein said at least one radioactive isotope of iodine is selected from the group of $^{122}I$, $^{123}I$, $^{125}I$, and $^{131}I$.

8. A method of therapeutically treating a living being comprising administering to the living being a physiologically effective amount of a compound as claimed in claim 6.

9. The compound of claim 6 wherein said compound is 1-iopanoyl-2-palmitoyl-rac-glycerol.

10. The compound of claim 6 wherein said compound is 1-[15-(m-iodophenyl)pentadecanoyl]-2-acetyl-rac-glycerol.

11. The compound of claim 6 wherein said compound is 1-palmitoyl-2-desethyliopanoyl-rac-glycerol.

12. The compound of claim 6 wherein said compound is 1-octanoyl-2-[3-(m-iodophenyl)propanoyl]-rac-glycerol.

13. The compound of claim 6 wherein said compound is 1-acetyl-2-[15-(m-iodophenyl)-pentadecanoyl]-rac-glycerol.

14. The compound of claim 6 wherein said compound is 1-palmitoyl-2-iopanoyl-rac-glycerol.

* * * * *